United States Patent [19]

Gill et al.

[11] Patent Number: 4,546,659

[45] Date of Patent: Oct. 15, 1985

[54] ATMOSPHERIC AIR SAMPLE COLLECTION DEVICE

[75] Inventors: Bernard B. J. Gill; Joseph L. P. M. Yergeau, both of Downsview, Canada

[73] Assignee: Her Majesty the Queen in right of Canada, as represented by the Minister of National Defence, Ottawa, Canada

[21] Appl. No.: 596,910

[22] Filed: Apr. 5, 1984

[30] Foreign Application Priority Data

Apr. 8, 1983 [CA] Canada .................................. 425520

[51] Int. Cl.⁴ ............................................... G01N 1/24
[52] U.S. Cl. .................................. 73/864.62; 422/102
[58] Field of Search ........... 73/864.52, 864.34, 864.61, 73/864.62, 864.91; 422/83, 102, 119

[56] References Cited

U.S. PATENT DOCUMENTS

| | | | |
|---|---|---|---|
| 3,734,692 | 5/1973 | Lucker | 73/864.62 |
| 3,862,576 | 1/1975 | Pogorski | 73/864.62 |
| 4,338,826 | 7/1982 | Jacoby et al. | 73/864.62 |

Primary Examiner—S. Clement Swisher
Attorney, Agent, or Firm—Cushman, Darby & Cushman

[57] ABSTRACT

An envelope for the collection of atmospheric air samples for subsequent analysis. The envelope is formed of first and second opposed panels of flexible, gas impermeable material which are peripherally sealed to define a collection chamber therebetween. The envelope contains expandable means, such as a spring, movable from an original, compressed condition between the opposed panels to a subsequent, expanded condition whereby portions of the opposed panels are biased apart. A self-sealing septum is provided on the first panel for use in selectively establishing fluid communication, by means of a puncturing cannula, between the collection chamber and external atmospheric air whereby the expandable means moves from the compressed condition to an expanded condition and concurrently draws a sample of the external atmospheric air into the collection chamber. A guard plate can also be provided in the envelope between the expandable means and the second panel in a position subjacent the self-sealing septum to prevent the puncturing cannula from puncturing the second panel.

8 Claims, 2 Drawing Figures

ATMOSPHERIC AIR SAMPLE COLLECTION DEVICE

FIELD OF THE INVENTION

The present invention relates to a device for use in the collection of atmospheric air samples for subsequent analysis.

BACKGROUND OF THE INVENTION

There is a requirement, particularly in the field of environmental or occupational health atmosphere monitoring, for the collection of small samples of atmospheric air in a rapid and simple fashion in a device which is sufficiently economical to produce that disposal following a single use can be justified. Ideally, the device should be of sufficient simplicity that the atmospheric air sample can readily be taken by an essentially untrained person, or by an automated mechanical device, and be of sufficient durability that the device, following sample collection, can be shipped, without any special handling requirements, to a laboratory for analysis.

Canadian Pat. No. 898,193, issued Apr. 18, 1972, teaches a resilient metallic disk-like sampling device of bistable configuration having a fluid inlet/outlet, either in the form of a capillary tube or a small diameter aperture, communicating with an internal sample chamber. In one stable configuration, the expanded configuration, the opposed walls of the device are maximally spaced apart to define therebetween a chamber of maximum specified volume. In the other stable configuration, the collapsed configuration, the opposed walls of the device are minimally spaced apart to define therebetween a chamber of minimum specified volume. The device can be transformed from the expanded configuration to the collapsed configuration by appropriately squeezing the walls of the expanded configuration, with concurrent expelling of the contents of the chamber through the fluid inlet/outlet, such that one of the opposed walls collapses inwardly and "snaps" through an over center position to overlie the other wall in substantially abutting relationship. Conversely, the device can also be transformed from the collapsed configuration to the expanded configuration, again by appropriately squeezing the device to cause the collapsed wall to "snap" outwardly back through the over center position, during the course of which a vacuum is created in the expanding chamber which results in the intake of fluid through the fluid inlet/outlet. The device, due to the resiliency of the metallic construction, can be "snapped" between the expanded and collapsed configurations quite a number of times without rupture.

To collect a fluid sample with the device of Canadian Pat. No. 898,193, it is necessary to establish fluid communication between the fluid inlet/outlet of the device, itself in the collapsed configuration, and a fluid source to be sampled, whereupon the device is "snapped" to transform it into the expanded configuration containing the sample fluid which is drawn into the chamber as it expands. Presuming that analysis of the fluid sample is to be performed at a different location, or at a later time, etc., it is then necessary to appropriately seal the device to preserve the integrity of the fluid sample. Sealing, in the case of a capillary tube type of fluid inlet/outlet can be accomplished by crimping of the bore, whereas in the case of a small diameter aperture sealing can be accomplished by means of a drop of solder or, more preferably, by means of an adhesive metal tape.

A significant disadvantage of the device of Canadian Pat. No. 898,193 is that the cost of manufacture is too high to justify one-time use only. While the device is susceptible to re-use, the necessary cleaning/purging between uses does add to the overall cost of use.

A further disadvantage of the device of Canadian Pat. No. 898,193, as presently commercially available, is the necessity of the separate and additional step of sealing the device, by whatever means.

SUMMARY OF THE INVENTION

The present invention provides a relatively low cost, self-filling and self-sealing device for the collection of atmospheric air samples for subsequent analysis.

In one particular aspect the present invention provides an envelope for the collection of atmospheric air samples, said envelope being formed of first and second opposed panels of flexible, gas impermeable material peripherally sealed to define a collection chamber therebetween, said envelope containing expandable means movable from an original, compressed condition between said opposed panels to a subsequent, expanded condition whereby portions of said opposed panels are biased apart, and a self-sealing septum associated with said first panel for use in selectively establishing fluid communication between the collection chamber and external atmospheric air whereby said expandable means moves from the compressed condition to an expanded condition and concurrently draws a sample of said external atmospheric air into said collection chamber.

In another particular aspect the present invention provides an envelope for the collection of atmospheric air samples, said envelope being formed of first and second opposed panels of flexible, gas impermeable polyethylene terephthalate polyester film peripherally heat sealed to define a collection chamber therebetween, said envelope containing a centrally positioned stainless steel conical coil spring movable from an original, compressed condition between said opposed panels to a subsequent, expanded condition whereby portions of said opposed panels are biased apart, said envelope having a self-sealing polytetrafluoroethylene septum centrally affixed to the exterior surface of said first panel for use in selectively establishing fluid communication, by means of a puncturing cannula, between the collection chamber and external atmospheric air whereby said conical coil spring moves from the compressed condition to an expanded condition and concurrently draws a sample of said external atmospheric air into said collection chamber, said envelope further containing a stainless steel guard plate interposed between said conical coil spring and the second panel.

BRIEF DESCRIPTION OF THE DRAWINGS

In drawings which illustrate one embodiment of the present invention.

DETAILED DESCRIPTION OF THE INVENTION

Figure 1:
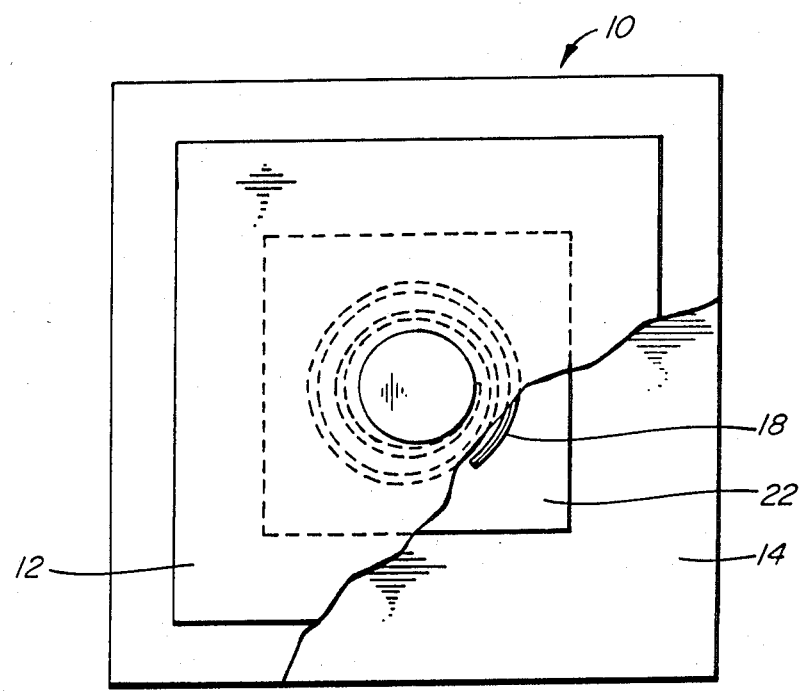
FIG. 1 is a top plan view, partially broken away, of an atmospheric air sample collection device according to the present invention.
Figure 2:
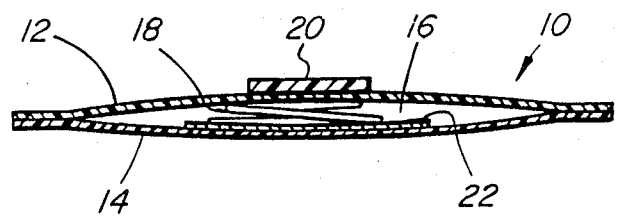
FIG. 2 is a cross-section through the atmospheric air sample collection device of FIG. 1, nominally illustrated in an expanded (filled) condition.

Referring now to FIGS. 1 and 2, the atmospheric air sample collection device includes an envelope 10 formed of opposed flexible first and second panels 12 and 14, respectively, which are peripherally sealed to define therebetween a collection chamber 16. Contained within the envelope 10 is an expandable means 18, which in the embodiment illustrated is in the form of a conical coil spring. A self-sealing septum 20 is provided on panel 12 for use in establishing fluid communication between the collection chamber 16 and external atmospheric air by means of a puncturing cannula. In the embodiment illustrated, a guard plate 22 has also been provided in the envelope to prevent inadvertent puncture of panel 14 by any puncturing cannula inserted through self-sealing septum 20.

The panels 12 and 14 can be formed of any flexible, gas impermeable material which is substantially inert to substituent components of an atmospheric air sample. Preferably, the material employed is susceptible to heat sealing so that the peripheral sealing of panels 12 and 14 can be readily and effectively accomplished. Various polyethylene terephthalate films satisfy these criteria; for example, Mylar ® has been found to be particularly suitable. Other satisfactory material will be obvious to those skilled in the art.

The expandable means 18 should likewise be formed of material which is substantially inert to constituent components of an atmospheric air sample. Where the expandable means 18 is a spring, be it a light duty conical coil spring as illustrated, or of some other suitable configuration, a satisfactory material is a stainless steel. A less preferred form of expandable means 18 is a block or pad of open-celled low density foam, for example a polyester foam having a density in the order of about 6 lbs/ft$^3$.

Various elastomeric materials can be employed for the self-sealing septum 20, as will also be well known to those skilled in the art. A Teflon ® (polytetrafluoroethylene) septum, attached to panel 12 by means of a silicon adhesive, has for example proven satisfactory.

The guard plate 22 must also be of a material substantially inert to substituent components of an atmospheric air sample, and again a stainless steel is exemplary of a suitable material.

The envelope 10, as manufactured, has minimal dead volume in the collection chamber 16 since air is pressed from between the panels 12 and 14, and the expandable means 18 concurrently compressed, at the time of peripherally sealing the panels 12 and 14. The envelope 10 and associated expandable means 18 remain in this compressed condition, by virtue of ambient pressure, until fluid communication between the collection chamber 16 and external atmospheric air is established by puncture of the self-sealing septum 20 by a puncturing cannula, whereupon the expandable means 18 expands to concurrently draw a sample of the external atmospheric air into the collection chamber 16. When the atmospheric air sample has been collected the puncturing cannula is simply withdrawn from the self-sealing septum 20 and the envelope is ready for content analysis. Analytical samples of the contents thereafter can readily be removed as desired from the envelope through the self-sealing septum 20 by means for example of a hypodermic needle and syringe.

A typical construction of the device of FIGS. 1 and 2, but without any limitative intentions since the dimensions are arbitrary and not in themselves critical, is as follows. Panels 12 and 14 are 10 cm × 10 cm panels of Mylar ® film, peripherally heat sealed together along a 1 cm border. Expandable means 18 is a 2.5 cm × 2.5 cm × 3.5 cm stainless steel light duty conical coil spring. Guard plate 22 is a 5 cm × 5 cm × 0.005 cm stainless steel plate. Self-sealing septum 20 is a Teflon ® disk of 2 cm diameter adhered to panel 12. The envelope 10 in compressed condition, i.e. as manufactured, has a maximum thickness in the order of about 3.5 mm. In expanded condition, i.e. following the drawing in of an atmospheric air sample, the volume of which is typically in the order of about 10 cm$^3$ to 15 cm$^3$, the envelope 10 has a maximum thickness in the order of about 5 mm to 8 mm.

Envelope 10 and the associated elements, as will be readily apparent, need not be of the express configuration shown in FIGS. 1 and 2. Opposed panels 12 and 14 can, for example, be of other geometric shapes such as circular, rectangular, triangular, etc. Similar considerations apply to the self-sealing septum 20 and guard plate 22.

The present invention thus provides a relatively economical, self-filling and self-sealing device for the collection of atmospheric air samples for subsequent analysis. The device is susceptible to use in any number of air sampling situations in the environmental and occupational health fields.

It is not intended that the present specification be construed limitatively since numerous variations and modifications falling within the true broad spirit and scope of the invention will be obvious to persons skilled in the art.

The embodiments of the invention in which an exclusive property or privilege is claimed are defined as follows:

1. An envelope for the collection of atmospheric air samples, said envelope being formed of first and second opposed panels of flexible, gas impermeable material peripherally sealed to define a collection chamber therebetween said flexible, gas impermeable material being substantially inert to constituent components of an atmospheric air sample, said envelope containing expandable means movable from an original, compressed condition between said opposed panels to a subsequent, expanded condition whereby portions of said opposed panels are biased apart, a self-sealing septum associated with said first panel for use in selectively establishing fluid communication between the collection chamber and external atmospheric air whereby said expandable means moves from the compressed condition to an expanded condition and concurrently draws a sample of said external atmospheric air into said collection chamber, and a guard plate contained in said envelope between the expandable means and the second panel in a position subjacent the self-sealing septum.

2. An envelope according to claim 1, wherein said expandable means is a coil spring which is axially aligned substantially normal to the nominal plane of the opposed panels.

3. An envelope according to claim 2, wherein said coil spring is a conical coil spring.

4. An envelope according to claim 2, wherein said guard plate and said coil spring are comprised of a stainless steel.

5. An envelope according to claim 4, wherein said coil spring is a conical coil spring.

6. An envelope according to claim 1, wherein said expandable means is a pad of an open-celled low density foam of a material which is substantially inert to constituent components of an atmospheric air sample.

7. An envelope according to claim 1, wherein said self-sealing septum is substantially centered on the exterior surface of said first panel.

8. An envelope for the collection of atmospheric air samples, said envelope being formed of first and second opposed panels of flexible, gas impermeable polyethylene terephthalate polyester film peripherally heat sealed to define a collection chamber therebetween, said envelope containing a centrally positioned stainless steel conical coil spring movable from an original, compressed condition between said opposed panels to a subsequent, expanded condition whereby portions of said opposed panels are biased apart, said envelope having a self-sealing polytetrafluoroethylene septum centrally affixed to the exterior surface of said first panel for use in selectively establishing fluid communication, by means of a puncturing cannula, between the collection chamber and external atmospheric air whereby said conical coil spring moves from the compressed condition to an expanded condition and concurrently draws a sample of said external atmospheric air into said collection chamber, said envelope further containing a stainless steel guard plate interposed between said conical coil spring and the second panel.

* * * * *